US008105987B2

(12) United States Patent
Acosta et al.

(10) Patent No.: US 8,105,987 B2
(45) Date of Patent: *Jan. 31, 2012

(54) CORROSION INHIBITORS FOR AN AQUEOUS MEDIUM

(75) Inventors: Erick J. Acosta, Sugar Land, TX (US); Jeffery Caleb Clark, Sugar Land, TX (US)

(73) Assignee: Nalco Company, Naperville, IL (US)

( * ) Notice: Subject to any disclaimer, the term of this patent is extended or adjusted under 35 U.S.C. 154(b) by 337 days.

This patent is subject to a terminal disclaimer.

(21) Appl. No.: 12/245,806

(22) Filed: Oct. 6, 2008

(65) Prior Publication Data

US 2010/0084611 A1   Apr. 8, 2010

(51) Int. Cl.
C09K 8/54 (2006.01)
C09K 15/16 (2006.01)
C23F 11/00 (2006.01)
C23F 11/04 (2006.01)
C23F 11/14 (2006.01)

(52) U.S. Cl. .......... 507/240; 507/239; 507/243; 422/12; 422/16; 252/389.62; 252/390; 252/400.62; 252/401; 252/405; 252/394; 106/14.16; 106/14.26

(58) Field of Classification Search .............. 422/12, 422/16; 252/389.62, 390, 391, 392, 400.62, 252/401, 402, 403; 106/14.16, 14.26; 507/239, 507/240, 243
See application file for complete search history.

(56) References Cited

U.S. PATENT DOCUMENTS

| 2,980,657 | A | * | 4/1961 | Melamed | 526/307 |
|---|---|---|---|---|---|
| 3,167,554 | A | * | 1/1965 | Ernst | 544/357 |
| 3,260,669 | A | * | 7/1966 | Schoen | 507/243 |
| 3,932,296 | A | * | 1/1976 | Byth | 507/240 |
| 4,253,886 | A | * | 3/1981 | Aonuma et al. | 148/105 |
| 4,515,658 | A | * | 5/1985 | Fong | 162/168.4 |
| 4,699,951 | A | * | 10/1987 | Allenson et al. | 525/194 |
| 4,762,627 | A | * | 8/1988 | Martinez et al. | 507/203 |
| 4,784,796 | A | * | 11/1988 | Treybig et al. | 252/392 |
| 4,802,992 | A | * | 2/1989 | Fong et al. | 210/709 |
| 4,980,378 | A |   | 12/1990 | Wong et al. | |
| 5,798,023 | A | * | 8/1998 | Pruszynski et al. | 162/181.1 |
| 5,922,653 | A | * | 7/1999 | Ahmed et al. | 507/242 |
| 6,051,670 | A | * | 4/2000 | Ahmed et al. | 526/263 |
| 6,217,778 | B1 | * | 4/2001 | Shing et al. | 210/708 |
| 2003/0209499 | A1 | * | 11/2003 | Haase | 210/728 |
| 2006/0094913 | A1 |   | 5/2006 | Spratt | |
| 2010/0084612 | A1 | * | 4/2010 | Acosta et al. | 252/392 |
| 2010/0087338 | A1 | * | 4/2010 | Acosta | 507/90 |

(Continued)

FOREIGN PATENT DOCUMENTS

WO   2004032824   4/2004

(Continued)

OTHER PUBLICATIONS

Synthesis, Authors: Yadav, J.S et al. 2007 No. 22 pp. 3447-3450.*
Sharma et al, "Green and mild protocol for hetero-Michael addition of sulfur and nitrogen nucleophiles in ionic liquid", Journal of Molecular Catalysis, A: Chemical, 277, 2007, pp. 215-220.

(Continued)

*Primary Examiner* — Joseph D Anthony

(74) *Attorney, Agent, or Firm* — Edward O. Yonter; Michael B. Martin

(57) ABSTRACT

One or more methods for inhibiting corrosion in an aqueous medium that contain a composition with a specified generic formula are disclosed. The aqueous medium can be contained in an oil or gas pipeline or refinery.

17 Claims, 1 Drawing Sheet

U.S. PATENT DOCUMENTS

2010/0087339 A1* 4/2010 Acosta ............................ 507/90
2010/0219379 A1* 9/2010 Acosta et al. ................. 252/392
2010/0240618 A1* 9/2010 Pennell et al. ................ 514/150

FOREIGN PATENT DOCUMENTS

WO 2008089262 7/2008

OTHER PUBLICATIONS

V. Fedi et al, Inseration of an Aspartic Acid Moiety into Cyclic Pseudopeptides: Synthesis and Biological Characterization of Potent Antagonists for the Human Tachykinin NK-2 Receptor, Journal of Medicinal Chemistry, vol. 47, 2004, pp. 6935-6947.

* cited by examiner

CORROSION INHIBITORS FOR AN AQUEOUS MEDIUM

FIELD OF THE INVENTION

The field of the invention pertains to corrosion inhibitors for an aqueous medium, e.g. an aqueous medium in an oil and gas pipeline or refinery.

BACKGROUND OF THE MENTION

Corrosion of metal surfaces in an aqueous medium has long been a problem for the oil and gas industry. It is well known that during the production of oil and gas several other corrosive components are present such as brines, organic acids, carbon dioxide, hydrogen sulfide, and microorganisms. These aggressive constituents can cause severe corrosion to metal pipes, which are often made of low-alloy steels. This problem is even more troublesome in deep-sea operations where replacement of corroded equipment is difficult and costly. Therefore, it is common practice to employ corrosion inhibitors during the production, transportation, storage, and separation of crude oil and natural gas.

Corrosion inhibitors are usually surface-active compounds that form protective coatings on the surface of metal components, which come in contact with corrosive environments, and thus suppress corrosion. Common corrosion inhibitors are composed of amines, condensation products of fatty acids with polyamines, e.g. imidazolines, or quaternary ammonium compounds. Among the most frequently used corrosion inhibitors in crude oil and natural gas extraction are imidazoline derivatives. Alternative corrosion inhibitors that can be used alone or in combination with known corrosion inhibitors are being sought by the industry.

SUMMARY OF THE INVENTION

The present invention provides for a method of inhibiting corrosion in an aqueous medium comprising: adding to the aqueous medium an effective corrosion inhibiting amount of a synergist, a synergist when $H_2S$ is present in the aqueous medium, or no synergist when $H_2S$ is present in the aqueous medium, and a composition comprising the following formula and optionally salts thereof:

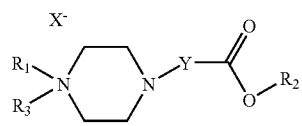

where $R_1$ is $C_nH_{2n+1}$, wherein n=0 to 12; benzyl; or H;
where $R_2$ is a $C_1$ to $C_{22}$ alkyl;
where $R_3$ is $C_nH_{2n+1}$, wherein n=0 to 12; benzyl; or H;
where $X^-$ is a halogen or a carboxylate and wherein $X^-$ is only present when both $R_1$ and $R_3$ are present;
where $Y=(CH_2)_n$, wherein n is 1 to 8; and
wherein $R_3$ and $R_1$ cannot be hydrogen at the same time.

The present invention also provides for a method of inhibiting corrosion in an aqueous medium comprising: adding to the medium an effective corrosion inhibiting amount of a synergist, a synergist when $H_2S$ is present in the aqueous medium, or no synergist when $H_2S$ is present in the aqueous medium, and a composition comprising the following formula and optionally salts thereof:

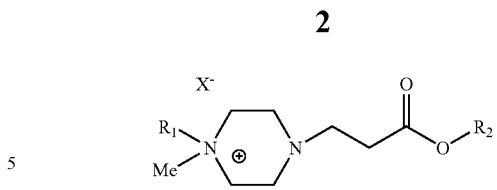

where $R_1$ is $C_nH_{2n+1}$, wherein n=0 to 12; benzyl; or H;
where $R_2$ is $C_nH_{2n+1}$, wherein n=1 to 22;
where X=Cl, Br, or I

DETAILED DESCRIPTION OF THE INVENTION

Figure 1:
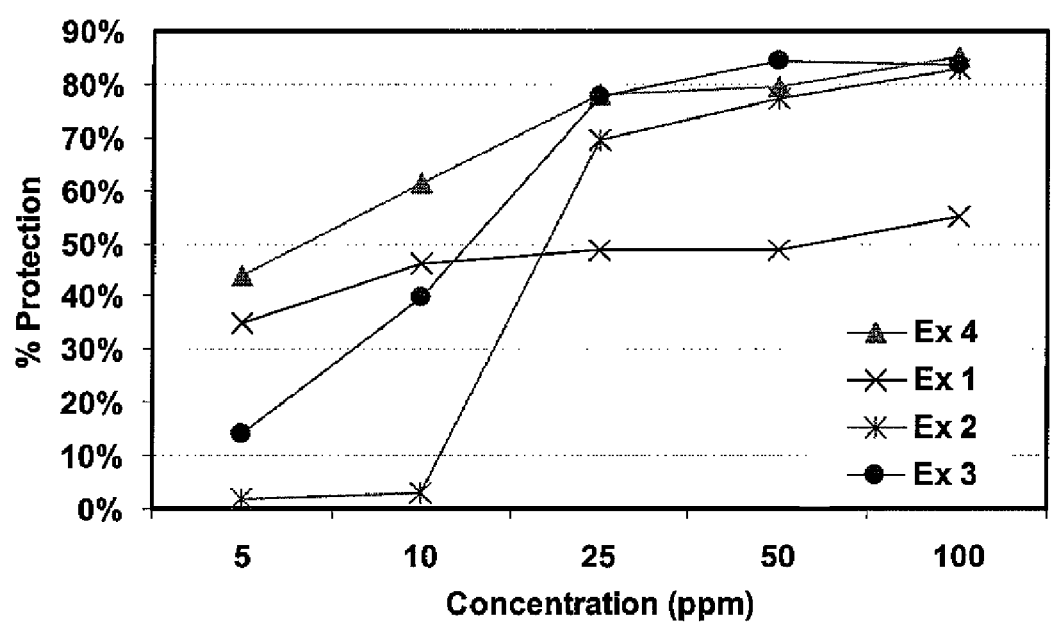
FIG. 1 shows corrosion inhibition results for Examples 1 to 4, which are found in Example section II.

The methodology described above can have various embodiments.

In one embodiment the alkyl groups of $R_1$ and/or $R_2$ are linear, branched, cyclic, and/or unsaturated.

In another embodiment, $R_3$ is a methyl or ethyl group. In further embodiment, $R_3$ has a linear conformation.

In another embodiment, the halogen is chlorine, bromine, or iodine. The halogen is in ionic form when it is associated with the composition.

In another embodiment, $Y=(CH_2)_n$, wherein n is 1 to 4, optionally wherein Y is linear or branched. When n=1, Y can not be branched.

In another embodiment, $R_1$ is a $C_4$-$C_6$ alkyl.
In another embodiment, $R_2$ is a $C_6$-$C_{12}$ alkyl.
In another embodiment, the composition comprises the following formula and optionally salts thereof:

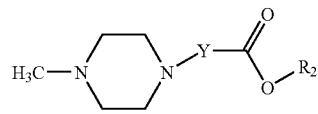

In another embodiment, the composition comprises the following formula:

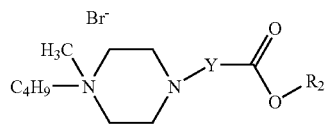

In another embodiment, the composition comprises the following formula:

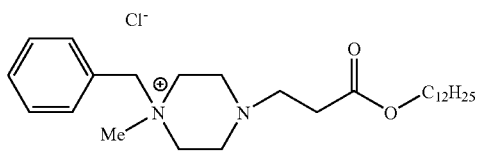

The compositions encompassed by this disclosure are applied to an aqueous medium that contains various levels of salinity.

In one embodiment, the aqueous medium that has a salinity of 1% to 20% weight/weight (w/w) total dissolved solids (TDS).

The aqueous medium to which the composition is applied to can contain various levels of water cut. One of ordinary skill in the art would interpret water cut to mean the percentage of water in a composition containing an oil and water mixture.

In one embodiment, the water cut is from 0% to 100% volume/volume (v/v).

In another embodiment, the water cut is from 1% to 60% v/v.

Various synthesis methodologies, which can be appreciated by one of ordinary skill in the art, can be utilized to make the claimed compositions. These compositions are then utilized in methods of inhibiting corrosion. The compositions can be made in the presence of a synergist.

In one embodiment, a composition is prepared by reacting an alkyl acrylate with 1-methylpiperazine.

In a further embodiment, the acrylate is a lauryl acrylate.

In another embodiment, the composition contains a quaternary ammonium salt prepared by reacting dodecyl 3-(4-methylpiperazin-1-yl) with an alkyl or a benzyl halide.

The compositions of this invention can contain one or more additional chemistries. Various formulations can be appreciated by one of ordinary skill in the art and can be made without undue experimentation. For example, crude mixtures of varied alkyl distributions are encompassed by this invention.

In one embodiment, the composition further comprises one or more hydrate inhibitors.

In another embodiment, the composition further comprises one or more thermodynamic hydrate inhibitors, one or more kinetic hydrate inhibitors, one or more anti-agglomerants, or a combination thereof.

In another embodiment, the composition further comprises one or more asphaltene inhibitors, paraffin inhibitors, corrosion inhibitors, scale inhibitors, emulsifiers, water clarifiers, dispersants, emulsion breakers, or a combination thereof.

In another embodiment, the composition further comprises one or more polar or non-polar solvents or a mixture thereof.

In another embodiment, the composition further comprises one or more solvents selected from isopropanol, methanol, ethanol, heavy aromatic naptha, toluene, ethylene glycol, ethylene glycol monobutyl ether (EGMBE), diethylene glycol monoethyl ether, xylene, or a combination thereof.

The aqueous medium in which the compositions and/or formulations are applied to can be contained in many different types of apparatuses, especially those that transport an aqueous medium from one point to another point, e.g. in one embodiment, the aqueous medium is contained in an oil and/or gas pipeline.

In another embodiment, the aqueous medium in which the compositions and/or formulations are applied to is in contact with many different types of surfaces that are capable of corrosion, e.g. those in an oil and gas pipelines/refineries, e.g. separation vessels, dehydration units, gas lines, and pipelines; and cooling water systems.

In another embodiment, the compositions and/or formulations are applied to industrial water systems and/or municipal water systems.

The compositions of the present disclosure and/or formulations thereof can be applied to an aqueous medium in various ways that would be appreciated by of ordinary skill in the art. One of ordinary skill in the art would appreciate these techniques and the various locations to which the compositions or chemistries can be applied.

In one embodiment, the compositions and/or formulations are pumped into the oil/gas pipeline by using an umbilical line. In a further embodiment, capillary injection systems can be utilized to deliver the surfactants, in this case corrosion inhibitors. U.S. Pat. No. 7,311,144 provides a description of an apparatus and methods relating to capillary injection, which is herein incorporated by reference.

Various dosage amounts of a composition and/or formulation can be applied to the aqueous medium to control corrosion. One of ordinary skill in the art would be able to calculate the amount of corrosion inhibitor for a given situation, e.g. content of aqueous medium, without undue experimentation.

In one embodiment, the dose range for the corrosion inhibitor that is applied to aqueous medium, e.g. aqueous medium contained in an oil/gas pipeline, is between 0.1% vol to 2% vol based on water cut.

Various types of synergists may be added to the aqueous medium in combination with the composition(s) described above. One of ordinary skill in the art could appreciate how to formulate a synergist and the composition.

In one embodiment, a synergist, a synergist when $H_2S$ is present in the aqueous medium, or no synergist when $H_2S$ is present in the aqueous medium is added to the aqueous medium with the compositions described above.

In another embodiment, the synergist can be a mercaptoethanol, e.g. 2-mercaptoethanol.

In another embodiment, the synergist formulation contains 3.5% v/v of 2-mercaptoethanol and 20% actives of the corrosion inhibitor composition described above.

In another embodiment, the synergist is a sulfur-containing synergist.

In another embodiment, the synergist contains a thiosulfate.

The examples are not meant to be limiting.

EXAMPLE SECTION

I. Synthesis Strategies for Corrosion Chemicals

A. Synthesis of dodecyl 3-(4-methylpiperazin-1-yl)propanoate

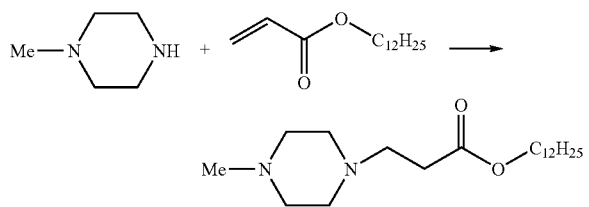

In a 40-mL scintillation vial, 12.0 g (0.05 moles) of lauryl acrylate are charged followed by the slow addition of 5.0 g (0.05 moles) of 1-methyl piperazine. The mixture is agitated using a magnetic stirrer bar and heated to 85° C. for at least 16 hours using a heating block. The final product is a light brown liquid at ambient temperature. Complete conversion is apparent from the lack of olefin protons in the $^1$H-NMR spectra. $^1$H-NMR (300 MHz, CDCl3): δ 3.83 (t, 6.6 Hz, 2H), 2.45 (t, 7.3 Hz, 2H), 2.24 (m, 10H), 2.02 (s, 3H), 1.38 (t, 6.8 Hz, 2H), 1.03 (m, 18H), 0.65 (t, 7.1 Hz, 3H). $^{13}$C-NMR (75 MHz, CDCl3): δ 171.78, 63.92, 54.64, 53.12, 52.39, 45.53, 31.93, 31.45, 29.19, 21.17, 29.12, 29.08, 28.89, 28.80, 28.20, 25.47, 22.20, 13.63.

B. Sythesis of 1-butyl-4-(3-(dodecyloxy)-3-oxopropyl)-1-methylpiperazin-1-ium bromide

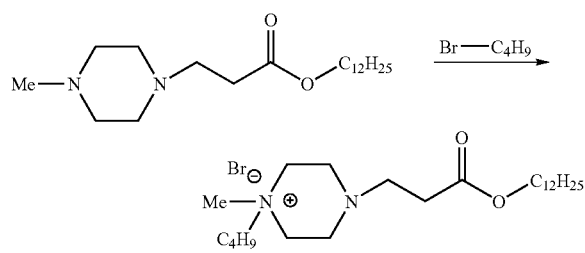

In a 100-mL round bottom flask, 5.0 g (0.015 moles) of dodecyl 3-(4-methylpiperazin-1-yl)propanoate and 7.3 g (0.044 moles) of butyl bromide are combined with 10 mL of isopropyl alcohol. This solution is heated to reflux overnight. Thin layer chromatography (TLC) was used to monitor the progress of the reaction with 1:1 methanol/toluene as a mobile phase and iodine to reveal the components on the plate. After the reaction is complete, the solvent and excess of butyl bromide are evaporated under vacuum. Finally, the resulting solid is dried under vacuum at 120° C. $^1$H-NMR (300 MHz, CDCl3): δ 3.92 (t, 5.9Hz, 2H), 3.76 (m, 2H), 3.56 (m, 4H), 3.35 (s, 3H), 2.91 (m, 6H), 2.46 (t, 6.6 Hz, 2H), 1.67 (m, 2H), 1.47 (m, 2H), 1.12 (m, 24H), 0.74 (m, 6H). $^{13}$C-NMR (75 MHz, CDCl3): δ 170.98, 64.61, 59.14, 51.84, 45.88, 31.44, 31.28, 30.81, 29.18, 29.16, 29.13, 29.08, 28.87, 28.81, 28.11, 25.50, 25.43, 22.21, 21.96, 21.60, 13.66, 13.49.

Examples 1-2, described below, were prepared by reacting 1-ethyl piperazine with various alkyl acrylates. Specifically, Examples 1-2 are quaternary ammonium salts prepared from the reaction of the tertiary amine and 1-bromobutane in isopropyl alcohol at a concentration of 80% w/w solids. After the reactions were completed, as determined by TLC, the final product was diluted to 60% w/w active ingredient with methanol.

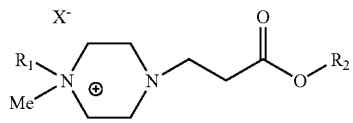

| Example | n | $R_1$ | X | Solvent |
|---|---|---|---|---|
| 1 | 8 (branched, 2-ethyl hexyl) | —C4H9 | Br | IPA/MeOH |
| 2 | 12 | —C4H9 | Br | IPA/MeOH |

II. Experimental Section

A. Composition of Corrosion Inhibitor where $R_1$ is $C_nH_{2n+1}$, wherein n=0 to 12; benzyl; or H;
where $R_2$ is $C_nH_{2n+1}$, wherein n=1 to 22;
where X=Cl, Br, or I B. Sample Preparation Each of the examples were prepared by dissolving the corrosion inhibitor to a 20% active into isopropanol and formulating it with a mercaptan synergist, 2-mercaptoethanol (3.5% 2-mercaptoethanol; other levels of synergist can be used, but this is the amount used for the experiments). Each of the examples exhibited solubility in isopropanol and was tested in a wheel box test. This test provides an indication of how a corrosion inhibitor will perform over a range of dosages.

C. Wheel Box Test Procedure

In order to test each of the examples, wheel box testing from NACE (National Association of Corrosion Engineers) publication ID182 (December 1982) were performed. The wheel box test is a test that is often used in the field of corrosion to compare the performance of a corrosion inhibitor to another. The following standard set of conditions were used to test corrosion inhibitor performance:

a. Temperature=176° F.;
b. Oil=10% LVT-200;
c. Brine=90% ASTM Seawater brine;
d. $CO_2$ Saturated;
e. Test Duration=24 hrs; and
f. Inhibitor Dosage=5, 10, 25, 50, 100 ppm based on total fluids The performance of the corrosion inhibitors was evaluated relative to an average corrosion rate of three untreated samples. These untreated bottles exhibit much higher corrosion rates than the treated bottles. This allows the corrosion inhibitors to be evaluated by their relative percent protection. As can be seen below, each of the above examples exhibits performance at dosages as low as 5 ppm and many perform increasingly well as the dosages approach 100 ppm.

D. Examples

| Example | $R_2$ | $R_1$ | X |
|---|---|---|---|
| 1 | —$C_{12}H_{25}$ | None | None |
| 2 | —$C_{12}H_{25}$ | —$C_4H_9$ | Br |
| 3 | —$C_{12}H_{25}$ | —$C_6H_{13}$ | Br |
| 4 | —$C_{12}H_{25}$ | Benzyl | Cl |

E. Corrosion Inhibition Results/Performance

Tables 1 to 4 show the results from the wheel box testing done for Examples 1 to 4. Example 1 is the only surfactant tested that does not contain a quaternary ammonium salt. This compound demonstrated good percent protection at low concentration (5-10 ppms), as well as at higher concentrations (25 to 100 ppms).

TABLE 1

Wheel Box testing results for corrosion inhibition using Example 1 at various concentrations.

| Concentration, ppm | % Protection |
|---|---|
| 5 | 35 |
| 10 | 46 |
| 25 | 49 |
| 50 | 49 |
| 100 | 55 |

Example 2 showed a minimal protection at low concentrations of chemical, but as the concentration is increased to 25 ppm, the protection suddenly jumps from 3% to 70%. The corrosion inhibition continued increasing as the concentration of surfactant was increased from 25 to 50 ppms. The best performance is observed at 100 ppm with an 83% protection.

TABLE 2

Wheel Box testing results for corrosion inhibition using Example 2 at various concentrations.

| Concentration, ppm | % Protection |
|---|---|
| 5 | 2 |
| 10 | 3 |
| 25 | 70 |
| 50 | 78 |
| 100 | 83 |

Example 3 shows significantly better protection than Example 2 at concentrations of 10 ppm or lower. Nevertheless, at 25 ppm to 100ppm Examples 2 and 3 have very similar corrosion inhibition performance, respectively. The best protection observed for Example 3 is 84% at a concentration of 100ppm.

TABLE 3

Wheel Box testing results for corrosion inhibition using Example 3 at various concentrations.

| Concentration, ppm | % Protection |
|---|---|
| 5 | 14 |
| 10 | 40 |
| 25 | 78 |
| 50 | 84 |
| 100 | 84 |

The best overall performance is obtained with Example 4. Excellent protection is observed at both low and high concentrations of inhibitors. At a just 5 ppm concentration, 44% protection is observed while at 100 ppm the corrosion inhibition obtained is 85%. FIG. 1 shows a plot of a concentration of surfactants versus % protection for Examples 1 to 4.

TABLE 4

Wheel Box testing results for corrosion inhibition using Example 4 at various concentrations.

| Concentration, ppm | % Protection |
|---|---|
| 5 | 44 |
| 10 | 60 |
| 25 | 78 |
| 50 | 80 |
| 100 | 85 |

We claim:

1. A method of inhibiting corrosion in an aqueous medium comprising: adding to the medium an effective corrosion inhibiting amount of a synergist, a synergist when $H_2S$ is present in the aqueous medium, or no synergist when $H_2S$ is present in the aqueous medium, and a composition comprising the following formula and optionally salts thereof:

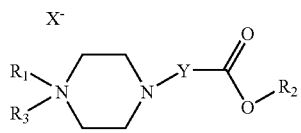

wherein $R_1$ is $C_nH_{2n+1}$, wherein n=0 to 12; benzyl; or H;
wherein $R_2$ is a $C_1$ to $C_{22}$ alkyl;
wherein $R_3$ is $C_nH_{2n+1}$, wherein n=0 to 12; benzyl; or H;
wherein $X^-$ is a halogen or a carboxylate and wherein $X^-$ is only present when both $R_1$ and $R_3$ are present;
wherein $Y=(CH_2)_n$, wherein n is 1 to 8; and
wherein $R_3$ and $R_1$ cannot be hydrogen at the same time.

2. The method of claim 1, wherein the alkyl groups of $R_1$ and/or $R_2$ are linear, branched, and/or cyclic.

3. The method of claim 1, wherein $R_3$ is a methyl or an ethyl group.

4. The method of claim 1, wherein the halogen is chlorine, bromine, or iodine.

5. The method of claim 1, wherein $R_1$ is a $C_4$-$C_6$ alkyl.

6. The method of claim 1, wherein $R_2$ is a $C_6$-$C_{12}$ alkyl.

7. The method of claim 1 wherein the composition comprises the following formula and optionally salts thereof:

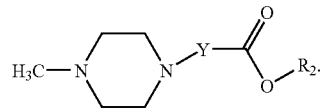

8. The method of claim 1 wherein the composition comprises the following formula:

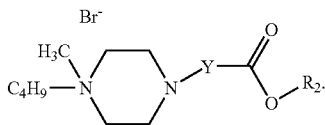

9. The method of claim 1 wherein the composition comprises the following formula:

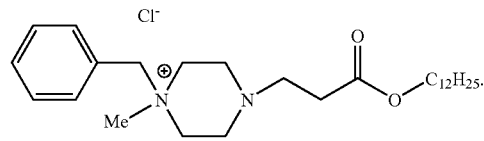

10. The method of claim 1, wherein the composition further comprises one or more hydrate inhibitors.

11. The method of claim 1, wherein the composition further comprises one or more thermodynamic hydrate inhibitors, one or more kinetic hydrate inhibitors, one or more anti-agglomerants, or a combination thereof.

12. The method of claim 1, wherein the composition further comprises one or more asphaltene inhibitors, paraffin inhibitors, corrosion inhibitors, scale inhibitors, emulsifiers, water clarifiers, dispersants, emulsion breakers, or a combination thereof.

13. The method of claim 1, wherein the composition further comprises one or more polar or nonpolar solvents or a mixture thereof.

14. The method of claim 1, wherein the composition further comprises one or more solvents selected from isopropanol, methanol, ethanol, heavy aromatic naptha, toluene, ethylene glycol, EGMBE, diethylene glycol monoethyl ether, xylene, or a combination thereof.

15. A method of inhibiting corrosion in an aqueous medium comprising adding to the medium an effective corrosion inhibiting amount of a synergist and a composition prepared by reacting an alkyl acrylate with 1-methylpiperazine.

16. The method of claim 15 wherein said acrylate is a lauryl acrylate.

17. A method of inhibiting corrosion in an aqueous medium comprising: adding to the medium an effective corrosion inhibiting amount of a synergist, a synergist when $H_2S$ is present in the aqueous medium, or no synergist when $H_2S$ is present in the aqueous medium, and a composition comprising the following formula and optionally salts thereof:

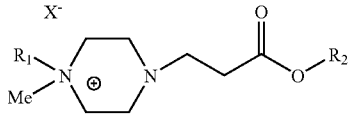

wherein $R_1$ is $C_nH_{2n+1}$, wherein n=0 to 12; benzyl; or H;
wherein $R_2$ is $C_nH_{2n+1}$, wherein n=1 to 22;
wherein X =Cl, Br, or I.

* * * * *